United States Patent
Roslaniec et al.

[11] Patent Number: 5,879,625
[45] Date of Patent: Mar. 9, 1999

[54] OPTICAL SELECTION AND COLLECTION OF DNA FRAGMENTS

[75] Inventors: Mary C. Roslaniec; John C. Martin; James H. Jett; L. Scott Cram, all of Los Alamos, N. Mex.

[73] Assignee: The Regents of the University of California, Los Alamos, N. Mex.

[21] Appl. No.: 951,955

[22] Filed: Oct. 17, 1997

Related U.S. Application Data

[62] Division of Ser. No. 632,743, Apr. 15, 1996, Pat. No. 5,707,808.

[51] Int. Cl.⁶ .............................. G01N 1/14; C12Q 1/68
[52] U.S. Cl. .............................. 422/50; 422/68.1; 435/6
[58] Field of Search .............. 422/50, 68.1; 435/6; 514/44

[56] References Cited

U.S. PATENT DOCUMENTS 4,395,397  7/1983  Shapiro .................................. 424/101

OTHER PUBLICATIONS

Tore Lindmo et al., "Flow Sorters for Biological Cells," *Flow Cytometry and Sorting*, Second Edition, pp. 145–169, Wiley–Liss, Inc. (1990).

Hans Herweijer et al., "High–Speed Photodamage Cell Selection Using Bromodeoxyuridine/Hoechst 33342 Photosensitized Cell Killing," Cytometry 9, 143 (1988.

Jan F. Keij et al., "High–Speed Photodamage Cell Selection Using A Frequency–Doubled Argon Ion Laser," Cytometry 19, 209 (1995).

Kathleen G. Specht, "The Role Of DNA Damage In PM2 Viral Inactivation By Methylene Blue Photosensitization," Photochem. and Photobiol. 59, 506 (1994).

G.T. Hirons et al., "TOTO and YOYO: New Very Bright Fluorochromes For DNA Content Analyses by Flow Cytometry," Cytometry 15, 1 (1994).

H.S. Rye et al. "Stable Fluorescent Complexes Of Double–Stranded DNA with Bis–Intercalating Asymmetric Cyanine Dyes: Properties And Applications," Nucleic Acids Res. 20, 2803 (1992).

Alexander N. Glazer et al., "Stable Dye–DNA Intercalation Complexes As Reagents For High–Sensitivity Fluorescence Detection," Nature 359, 859 (1992).

(List continued on next page.)

*Primary Examiner*—Ardin H. Marschel
*Attorney, Agent, or Firm*—Samuel M. Freund

[57] ABSTRACT

Optical selection and collection of DNA fragments. The present invention includes the optical selection and collection of large (>$\mu$g) quantities of clonable, chromosome-specific DNA from a sample of chromosomes. Chromosome selection is based on selective, irreversible photoinactivation of unwanted chromosomal DNA. Although more general procedures may be envisioned, the invention is demonstrated by processing chromosomes in a conventional flow cytometry apparatus, but where no droplets are generated. All chromosomes in the sample are first stained with at least one fluorescent analytic dye and bonded to a photochemically active species which can render chromosomal DNA unclonable if activated. After passing through analyzing light beam(s), unwanted chromosomes are irradiated using light which is absorbed by the photochemically active species, thereby causing photoinactivation. As desired chromosomes pass this photoinactivation point, the inactivating light source is deflected by an optical modulator; hence, desired chromosomes are not photoinactivated and remain clonable. The selection and photoinactivation processes take place on a microsecond timescale. By eliminating droplet formation, chromosome selection rates 50 times greater than those possible with conventional chromosome sorters may be obtained. Thus, usable quantities of clonable DNA from any source thereof may be collected.

3 Claims, 8 Drawing Sheets

OTHER PUBLICATIONS

Peter M. Goodwin et al., "Rapid Sizing Of Individual Fluorescently Stained DNA Fragments By Flow Cytometry," Nucleic Acids Research 21, 803 (1993).

Jeffrey T. Petty et al., "Characterization Of DNA Size Determination Of Small Fragments By Flow Cytometry," Anal. Chem. 67, 1755 (1995).

Kathy E. Yokobata et al., "Development Of A Plaque Reduction Assay And Application To The Study Of Psoralen–Damaged DNA," Photochem. and Photobiol. 43, 391 (1986).

T. T. Perkins et al., "Direct Observation of Tube–Like Motion of a Single Polymer Chain," Science 264, 819 (1994).

5,879,625

OPTICAL SELECTION AND COLLECTION OF DNA FRAGMENTS

This application is a divisional of application Ser. No. 08/632,743 filed on Apr. 15, 1996, now U.S. Pat. No. 5,707,808.

FIELD OF THE INVENTION

The present invention relates generally to the separation of chromosomes and, more particularly, to the high speed selection and collection of large (greater than microgram) quantities of chromosomal DNA (deoxyribonucleic acid) and/or DNA fragments by photochemical inactivation of unwanted chromosomes in a sample, with subsequent cloning of the spared DNA. This invention was made with government support under Contract No. W-7405-ENG-36 awarded by the U.S. Department of Energy to The Regents of the University of California. The government has certain rights in the invention.

BACKGROUND OF THE INVENTION

Continued study of the human genome and more recently the mouse genome has resulted in a clear need for sorting large numbers of chromosomes. The ability to identify, isolate and amplify specific genetic sequences is pivotal to genetic mapping, the search for DNA sequence probes, construction of chromosome-specific libraries, identification of disease genes, and understanding the basic genome organization. Since the human genome is comprised of 3 billion DNA base pairs distributed over 24 chromosome types, identification of a specific gene or gene mutation in this system is a complex undertaking. Chromosome sorting can be used to narrow the source of the DNA to a specific chromosome. By sorting human chromosomes prior to genetic mapping analysis, the complexity of the study is reduced by a factor of about 24. Sorted chromosomes have proven to be invaluable to the National Laboratory Gene Library Project for the construction of small insert libraries (up to 25 kb) prepared from bacteriophages and large insert libraries (35 kb to several hundred kb) prepared from cosmids and yeast artificial chromosomes (YACs).

Analysis of a single chromosome in a flow cytometer was first reported in 1975. Initially, a single fluorescent DNA probe was used to distinguish between chromosome types; however, by 1980, two-fluorochrome analysis of human chromosomes had been developed making it possible to resolve 20 of the 24 types of human chromosomes. Improvements in buffers, high speed sorting, slit scan analysis and data analysis, were subsequently made.

Chromosome sorting is currently achieved using commercial flow cytometers which rely on droplet sorting. Briefly, individual chromosomes stained with one or two fluorescent dyes pass through either one or two sequential focused laser beams tuned to excite the fluorescent stains. Optimally, each chromosome has a unique staining pattern allowing identification based on distinctive fluorescent characteristics such as fluorescence intensity. A liquid carrier stream is caused to break into droplets containing chromosomes. Droplets containing chromosomes of interest are charged. All droplets pass through an electric field and the charged droplets are deflected into a separate collection tube, thus sorting the chromosomes. See, e.g., "Flow Sorters for Biological Cells," by Tore Lindmo et al., *Flow Cytometry and Sorting*, Second Edition, Wiley-Liss, Inc.: New York, 1990; pages 145–169.

While flow cytometry is currently the principal technique used in sorting chromosomes, drawbacks persist; separation rates are limited by the rate of stable droplet formation. The degree of separation is inversely proportional to analysis rate, that is, the faster the sorting, the lower the purity. For example, in sorting chromosome no 4 of a hamster-human cell line (UV20 HL21-27), the purity is found to drop from 98 to 91% when the analysis rate is increased from 5000 to 18,000 chromosomes $s^{-1}$. Furthermore, in order to obtain high purity chromosomes, the probability of having more than one particle per drop must be extremely low; hence, particles are processed at approximately one-tenth the rate of droplet formation. Typical commercial sorters have analysis rates of approximately 1500 chromosomes $s^-$. This translates into sort rates of less than 50 chromosomes $s^-$. At this rate, about 60 hours of sorting time is required to obtain 1 $\mu$g of DNA. Sorting requirements for YAC cloning often require continuous around the clock sorting for as much as two weeks.

It is possible to achieve rates of the order of 200,000 droplets $s^{-1}$ in state-of-the-art flow cytometers, which translates to chromosome analysis rates in excess of 20,000 chromosomes $s^{-1}$. To achieve such high droplet rates, however, the sorter must operate at high pressure (200 psi) resulting in sorting instability and random chromosome damage. By reducing the pressure to about 120 psi, droplets can be produced at rates of 140,000 $s^{-1}$, improving sorting stability and reducing DNA degradation, but at the cost of lower chromosome throughput.

Methods of chromosome separation not relying on droplet formation would overcome the limitations associated with traditional sorting. In U.S. Pat. No. 4,395,397 for "Apparatus And Method For Killing Unwanted Cells," which issued to Howard M. Shapiro on Jul. 26, 1983, the removal of a subpopulation of unwanted cells from a flowing liquid stream containing a suspension of living cells is described. After detecting the presence of the unwanted cells, such cells are destroyed using a high-power laser. In "High-Speed Photodamage Cell Selection Using Bromodeoxyuridine/Hoechst 33342 Photosensitized Cell Killing," by Hans Herweijer et al., Cytometry 9, 143 (1988), the authors describe a photodamage cell sorter where unwanted cells detected by a first laser are destroyed by radiation from a second laser to which the unwanted cells are photosensitive. The radiation from the second laser is switched on and off (to permit desired cells to proceed unharmed through the apparatus) using an acoustoopic crystal. Cells are made photosensitive by growing the cells in the presence of 5-bromo-2'-deoxyuridine and staining with Hoechst 33342. A 400 mW ultraviolet light source is employed which permits 30,000 cells $s^{-1}$ to be sorted. Subsequent work in "High-Speed Photodamage Cell Selection Using A Frequency-Doubled Argon Ion Laser," by Jan F. Keij et al., Cytometry 19, 209 (1995), overcame the extreme photosensitivity of the stained cells and the 2–3 day culturing process for attaching the photosensitizer to the cells, by exploiting the intrinsic photosensitivity of the cellular DNA. Part of the far ultraviolet direct DNA damage is due to the production of thymidine dimers which hinder DNA replication in the cells. The short lifetime of the frequency-doubling crystals employed expected to be overcome using large argon ion lasers capable of emissions at 257–275 nm. In "The Role Of DNA Damage In PM2 Viral Inactivation By Methylene Blue Photosensitization," by Kathleen G. Specht, Photochem. and Photobiol. 59, 506 (1994), viral inactivation was observed as a result of phototreatment of viruses in which phenothiazines including methylene blue, toluidine blue and azure B were bound to nucleic acids in vitro.

TOTO and YOYO have been utilized for DNA analysis in flow cytometry. See, e.g., "TOTO and YOYO: New Very Bright Fluorochromes For DNA Content Analyses by Flow Cytometry," by G. T. Hirons et al., Cytometry 15, 1 (1994), "Stable Fluorescent Complexes Of Double-Stranded DNA with Bis-Intercalating Asymmetric Cyanine Dyes: Properties And Applications," by H. S. Rye et al., Nucleic Acids Res. 20, 2803 (1992), "Stable Dye-DNA Intercalation Complexes As Reagents For High-Sensitivity Fluorescence Detection," by Alexander N. Glazer and Hays S. Rye, Nature 359, 859 (1992), "Rapid Sizing Of Individual Fluorescently Stained DNA Fragments By Flow Cytometry," by Peter M. Goodwin et al., Nucleic Acids Research 21, 803 (1993), and "Characterization Of DNA Size Determination Of Small Fragments By Flow Cytometry," by Jeffrey T. Petty et al., Anal. Chem. 67, 1755 (1995). However, the ability of TOTO and YOYO to render the intercalated DNA unclonable has not been reported.

In "Development Of A Plaque Reduction Assay And Application To The Study Of Psoralen-Damaged DNA," by Kathy E. Yokobata et al., Photochem. and Photobiol. 43, 391 (1986), the photochemically induced reaction of a psoralen derivative with bacteriophage DNA is found to reduce the infectivity of the covalently modified DNA. This procedure is conducted in a bulk sample, and no separation of DNA fragments is taught or suggested.

Accordingly, it is an object of the present invention to provide a method for rapidly, but accurately selecting and collecting chosen strands of DNA from a mixture of DNA strands without requiring high-power, far-ultraviolet lasers and expensive dye removal steps.

Another object of the invention is to provide an apparatus for rapidly, but accurately rendering selected strands of DNA from a mixture of DNA strands unclonable without requiring high-power, far-ultraviolet lasers.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for separating a first group of DNA fragments from a second group of DNA fragments having characteristics which distinguish these fragments from the first group of DNA fragments, in a suspension thereof may include: permitting at least one photoinactivating molecule to bind with each DNA fragment in the suspension, distinguishing individual DNA fragments from the second group from those of the first group on the basis of the distinguishing characteristics, exposing individual DNA fragments from the second group to light which is absorbed by the at least one photoinactivating molecule bound thereto, whereby DNA fragments from the second group of chromosomes are inactivated and cannot be cloned, and cloning the DNA fragments from the first group, whereby the DNA fragments from the second group are separated from those from the first group.

In another aspect of the present invention in accordance with its objects and purposes, the apparatus for rendering unclonable a subpopulation of DNA fragments in a suspension of DNA fragments containing the subpopulation, where each of the fragments is bonded to at least one photoinactivating species, may include: means for detecting the presence of DNA fragments from the subpopulation in a flowing stream containing the suspension of DNA fragments such that signals are generated in response to the presence of DNA fragments from the subpopulation in the flowing stream, means, downstream from the detecting means and responsive to the generated signals, for producing pulses of light which are directed into a region of the flowing stream through which the individual DNA fragments pass and which are absorbed by the at least one photoinactivating molecule bound to the DNA fragments, whereby individual DNA fragments in the subpopulation thereof in the flowing stream are inactivated and cannot be cloned, and means for measuring the fluorescence intensity from the DNA fragments which are inactivated by the pulses of light from the light pulse producing means, such that the pulses of light may be accurately timed to substantially coincide with the arrival of the individual DNA fragments from the subpopulation thereof in the region in which the light pulses are directed.

Benefits and advantages of the present invention include rapidly, but accurately sorting and selecting chosen strands of DNA without requiring high-power, far-ultraviolet lasers and expensive dye removal steps.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings:

FIG. 1a is a schematic representation of the high-speed optical selection apparatus used to practice the method of the present invention, while

FIG. 2a shows predicted oscilloscope traces for the detected fluorescence signal from a stained DNA fragment as it passes through the detection region of the apparatus shown in FIGS. 1a and 1b hereof, the selection-decision output from a pulse generator in response to the correct fluorescence amplitude signal from a DNA fragment, the selection-decision signal processed in order to provide the acoustooptic modulator for the photoinactivation laser with the appropriate switching time and duration, and the detected signal from the selected DNA fragment as it passes through the light beam from the photoinactivating laser when the timing is correct, while

DETAILED DESCRIPTION

Briefly, the present invention includes the optical selection and collection of large (>µg) quantities of clonable, chromosome-specific DNA from a sample of chromosomes. Chromosome selection is based on selective, irreversible photoinactivation of unwanted chromosomal DNA. Although more general procedures may be envisioned, the invention is demonstrated by processing chromosomes in a conventional flow cytometry apparatus, but where no droplets are generated. All chromosomes in the sample are first stained with at least one fluorescent analytic dye and bonded to a photochemically active species which can render chromosomal DNA unclonable if photoactivated. After passing through analyzing light beam(s), unwanted chromosomes are irradiated using light which is absorbed by the photochemically active species, thereby causing photoinactivation. As desired chromosomes pass this photoinactivation point, the inactivating light source is deflected by an optical modulator; hence, desired chromosomes are not photoinactivated and remain clonable. The selection and photoinactivation processes take place on a microsecond timescale. By eliminating droplet formation, chromosome selection rates 50 times greater than those possible with conventional chromosome sorters may be obtained. Thus usable quantities of clonable DNA from any source thereof may be collected.

Figure 1A:
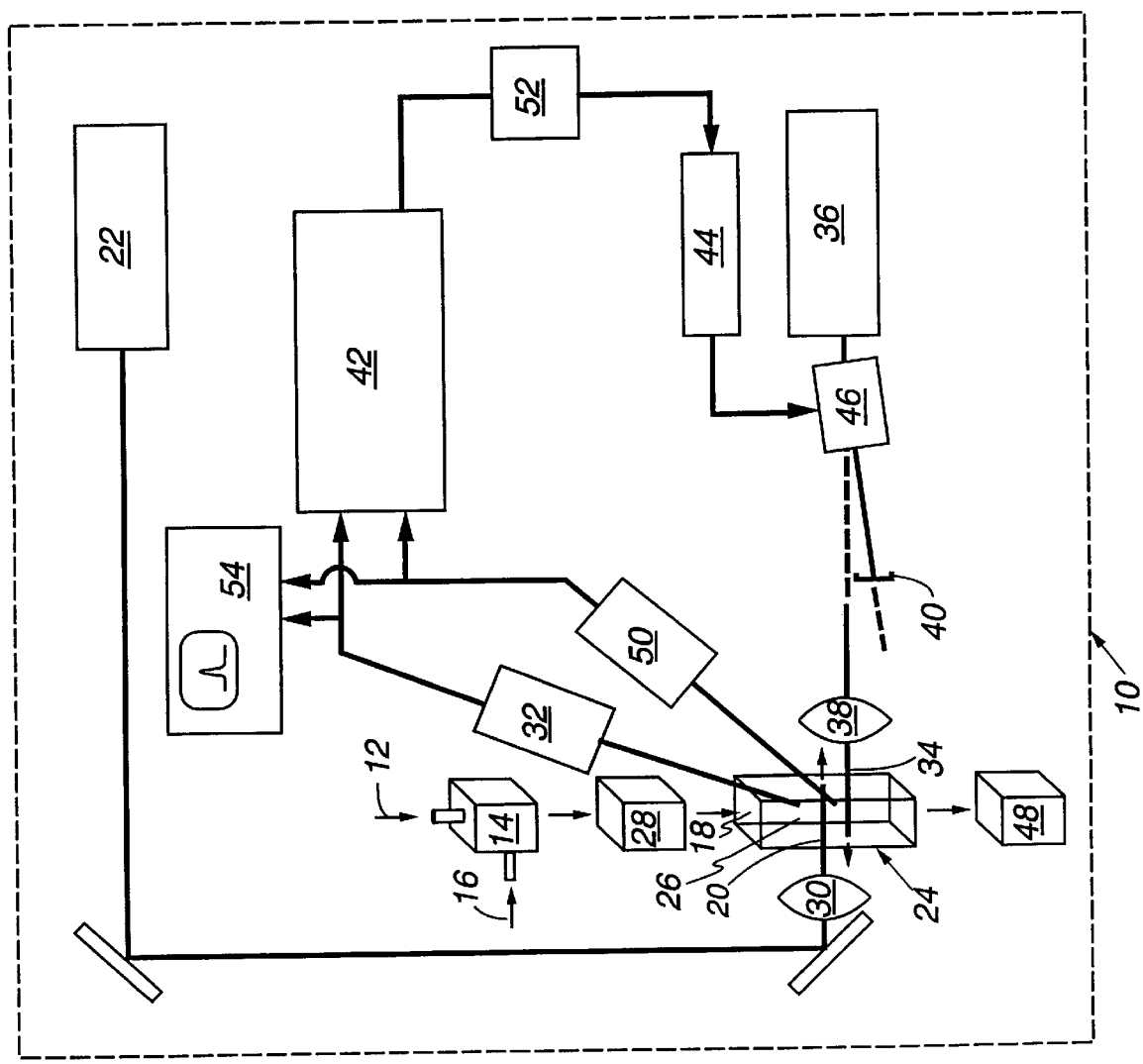
Figure 1B:
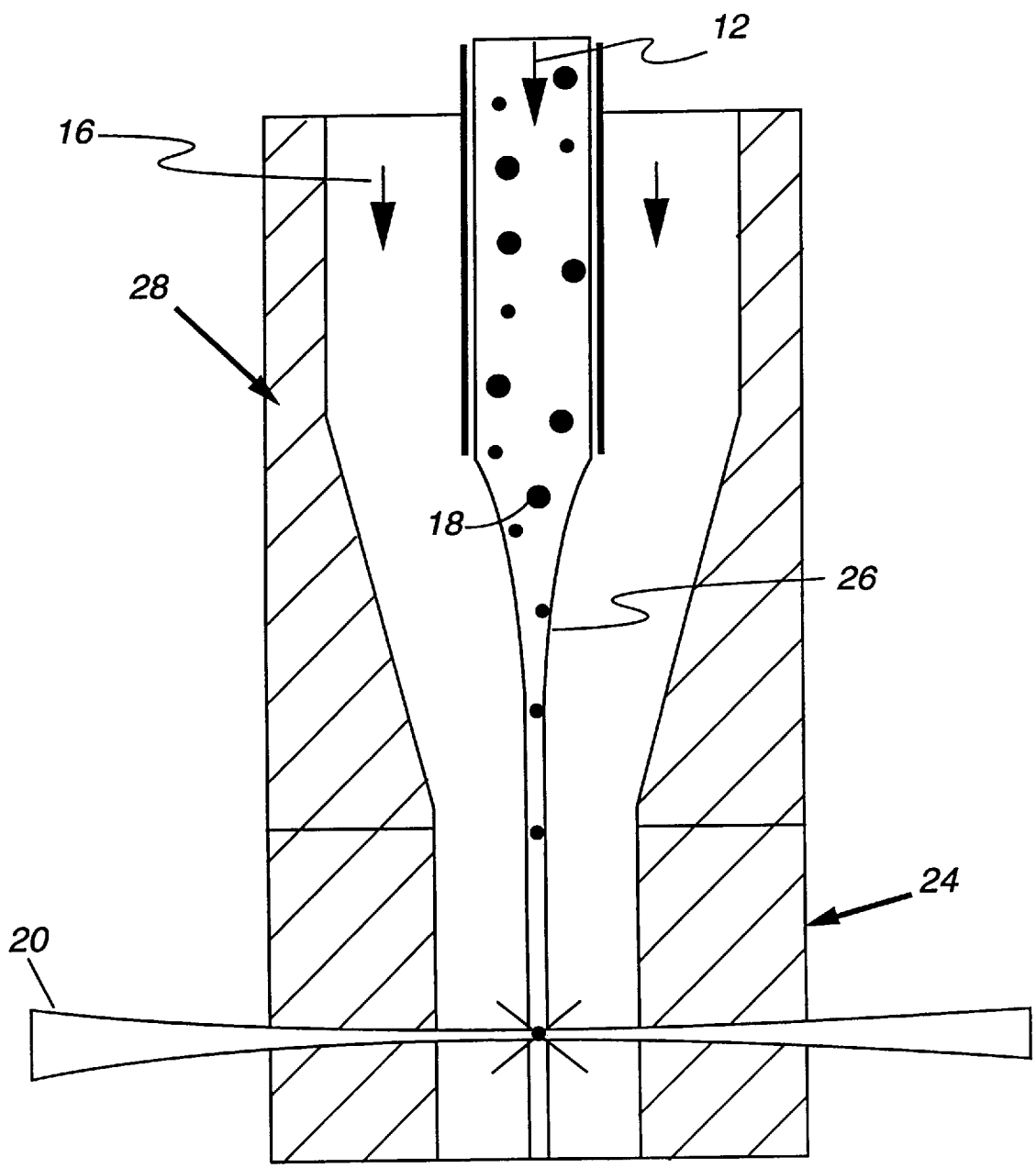
FIG. 1b is a schematic representation of the hydrodynamic focusing region shown in FIG. 1a hereof.

Reference will now be made in detail to the present preferred embodiments of the invention which are illustrated in the accompanying drawings. Similar or identical structural elements are identified using identical callouts. Turning now to FIG. 1, a schematic representation of the high-speed optical selection apparatus, 10, used to practice the method of the present invention is shown. Sample, 12, containing a suspension of chromosomes and/or DNA fragments in a suitable buffer is introduced into the inlet portion, 14, of the apparatus of the present invention along with sheath fluid, 16. The DNA fragment or chromosome concentration of the suspension is adjusted such that single DNA fragments or chromosomes, 18, are caused to flow through the output light beam, 20, from analytical laser, 22, in analytical and photoinactivation portion, 24, of apparatus 10 after the suspension is hydrodynamically focused into a dropletless flowing stream, 26, in focusing portion, 28, of the apparatus. Light beam 20 is focused using lens, 30. Chromosomes and DNA fragments are stained with fluorescent dyes which absorb the wavelength emitted by laser 22 before introduction to apparatus 10 and are analyzed as they pass through the light beam by detecting fluorescence therefrom using detector, 32. It should be mentioned that a second analytical laser might be employed for particle analysis in order to improve the selectivity of the particle selection process. Fluorescence from light excitation of the DNA fragments or chromosomes from this excitation would also be detected and analyzed. In situations where laser wavelengths, which are absorbed by the fluorescent analytical stains, are unavailable with suitable power, sources of light other than lasers might be employed. The principal difference between chromosomes is DNA content; that is, larger chromosomes contain more DNA base pairs. This difference alone permits some degree of selection. Chromosomes having more base pairs take up more dye, and the fluorescence signal therefrom is larger. In the present invention, chromosomes are selected on the basis of size. Some stains are base specific. For example, the Hoechst stain employed and described hereinbelow binds preferentially to AT regions, while chromomycin $A_3$ binds to GC rich regions. This allows separation not only based on size, but also based on base pair content. Chromosomes are stained with either or both dyes and analyzed with a one- or two-laser system, respectively. DNA fragments and/or chromosomes are also mixed with photoinactivating molecules which intercalate or otherwise bind thereto prior to, during, or after the analytical staining process, depending on the nature of the staining compounds and the photoinactivating molecules, before the suspension 12 thereof is introduced into the apparatus. Light, 34, from cw laser, 36, is focused using lens, 38, into the path of the flowing particles 18 downstream from the analytical region of portion 24 of the apparatus. As will be described in more detail hereinbelow, photoinactivation induced by the interaction of light 34 with the photonactivation molecules bound to the particles therein which prevents cloning of the chromosome-specific DNA or DNA particles subsequent to their exiting the apparatus. Since it is desired that photoinactivation only occur in selected particles in the flowing stream in response to the fluorescence signal detected by detector 32, light 34 is directed into the flowing stream of particles when an undesired particle is detected upstream and otherwise to beam stop, 40.

Processor/control unit, 42, achieves this function by directing acoustooptic modulator driver, 44, to switch modulator, 46, in response to signals from detector 32.

Photoinactivated particles and undamaged chromosomes and/or DNA fragments in flowing stream 26 exit portion 24 of apparatus 10 and are collected in collection vessel, 48, for further processing at a later time. It should be mentioned that other photolytic light sources may be envisioned in place of cw laser 36, including mercury and xenon arc lamps and pulsed lasers.

Since it is intended that photoinactivation of desired particles from light 34 be minimized, and the particle throughput of apparatus 10 maximized, light 34 is caused to intersect flowing stream 26 in only a small region for a small period of time. Therefore, small changes in sheath fluid and sample fluid pumping speeds will produce uncertainties in the position of the particles downstream after having been detected and selected. Moreover, changes in the mode character of the laser light will alter the location of the photoinactivation region. Therefore, scattered and fluorescence emission light resulting from the photoinactivation process is also detected. Detector, 50, achieves this purpose, and signals therefrom are directed to processor/controller 42 along with those from detector 32. The photodamage monitor may also include optics for collection of light generated by the presence of the photodamage beam (both scattered light and fluorescence), optical filters to block most, but not all of, the primary scattered photodamage light, and a photosensor to detect the light. Processor/controller 42 may then adjust the delay of the switching of acoustooptic modulator 46 by driver 44 through delay, 52. That is, the delay between the detection and analysis of fluorescence from an undesired particle and the direction of photoinactivating light 34 into flowing stream 26 is adjusted such that the fluorescence detected by detector 50 indicates that the undesired particle is near the center of the photoinactivating region. The duration of the period that photoinactivating light 34 crosses stream 26 may also be optimized. Presently, these adjustments are manually performed periodically; however, processor/controller 42 will ultimately take over this function. The relationship between the two detected signals may also be viewed in real time using oscilloscope, 54.

Figure 2A:
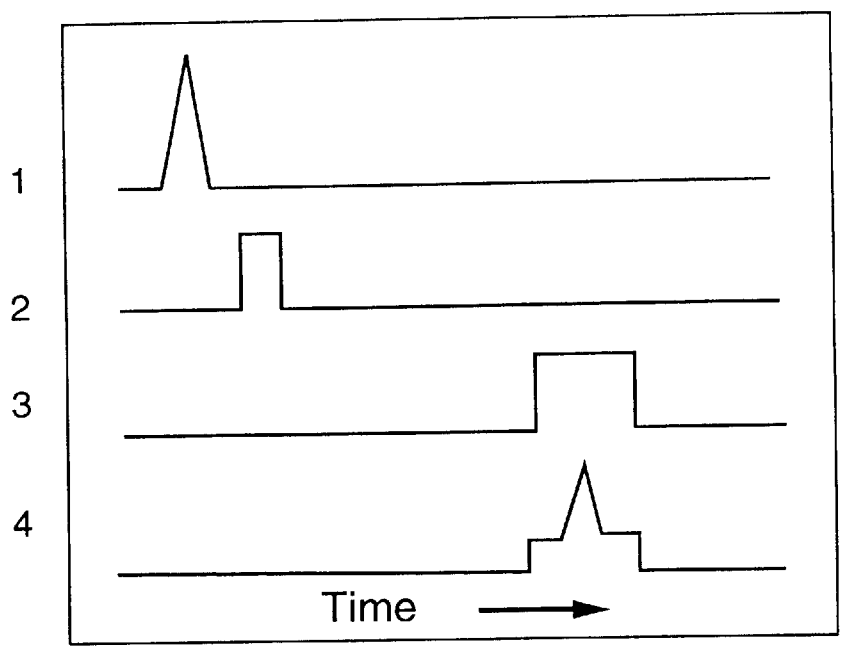
Figure 2B:
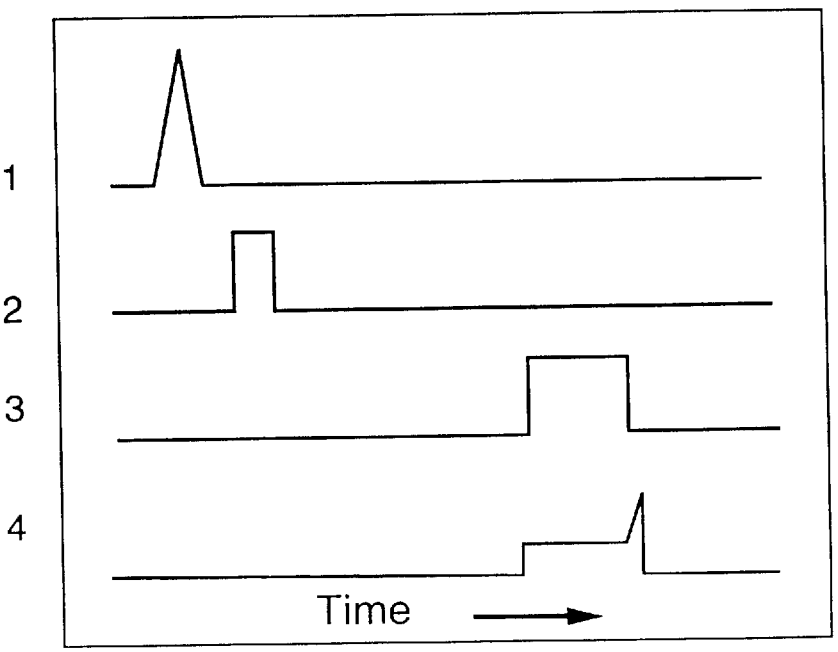
FIG. 2b shows the predicted oscilloscope traces for the same situation as illustrated in FIG. 2a hereof, except that the photodamage laser pulse is almost over when the DNA fragment enters the light beam from the photodamage laser.

FIGS. 2a and 2b illustrate predicted traces from oscilloscope 54 for the following signals: 1. from detector 32; 2. the output signal from processor/controller 42 in response thereto, which selects a particle to be photoinactivated; 3. the delayed and stretched signal from delay 52; and 4. the signal from detector 50 when the selected particle crosses the photoinactivation beam. The rectangular pedestal below the fluorescence peak in curve 4 represents scattered light from light beam 34. The fluorescence is shown to be from a particle in the center of the light beam. FIG. 2b shows the same predicted curves as those as in FIG. 2a, except that the delay for the firing of the photoinactivation laser is shown not to be adjusted correctly, and the photoinactivation pulse is nearly over by the time the particle enters the irradiation region in the flowing stream.

The present method is quite different from that applicable to cell photoselection, which induces nonspecific, metabolic or replication damage in viable cells and depends on the interruption of cell division. Cell photoselection techniques do not work for chromosome selection. Chromosome selection requires a specific, fast photochemical reaction to induce DNA photodamage at a large number of sites on each unwanted chromosome and is the key to the success of the present optical chromosome selector.

Photoinactivation can be achieved through direct far UV damage or indirectly with the use of a photosensitizing agent. One indirect approach requires UV light to photoinduce lethal adduct formation between psoralen derivatives and chromosomal DNA. A second indirect approach is likely to be a photooxidative process driven by visible light. Similar photochemistry and instrumentation can be used to purify DNA restriction fragments and mitochondrial DNA.

Figure 3:
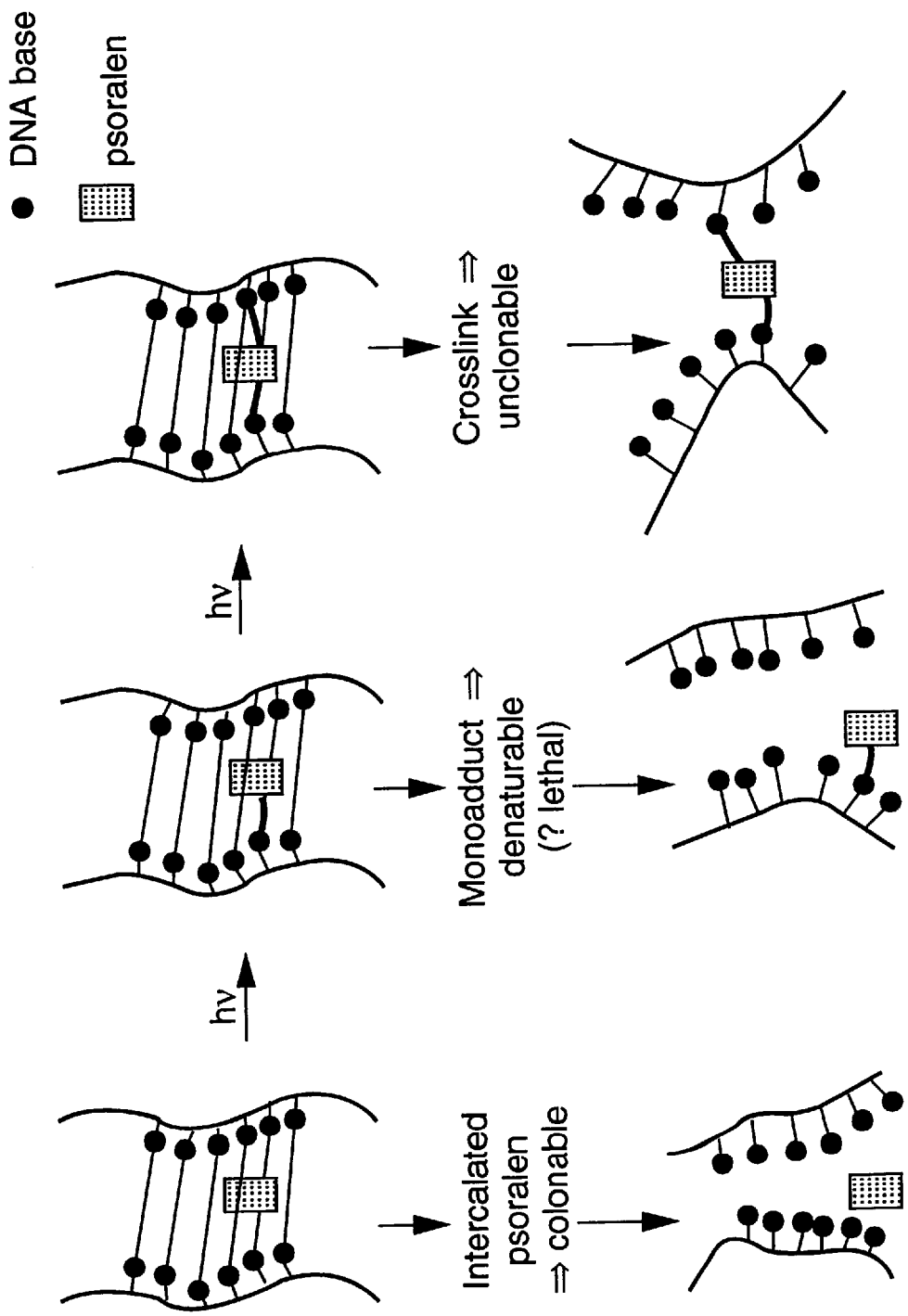
FIG. 3 is a schematic representation of the effects on clonability of psoralen adduct formation.

FIG. 3 illustrates the effects on clonability of intercalation of the DNA fragments and/or chromosomes by psoralen. Psoralen is known to reversibly intercalate between DNA strands in chromosomes. Rendering the chromosome-specific DNA or DNA from other sources unclonable is the basis for the DNA separation of the present invention.

The photochemistry of psoralens is well known See, e.g., "Recent Advances In Psoralen Phototoxicity Mechanism," by D. Averbeck, Photochem. Photobiol. 50, 859 (1989). Psoralens, also known as furocoumarins, are linear tricyclic heterocycles with a furan ring fused to a coumarin moiety. The initial interaction between DNA and psoralen is the noncovalent intercalation of the psoralen into the DNA double helix. Irradiation of the complex with near-UV light induces a cycloaddition reaction between the double bond of a pyrimidine base (predominately thymine) and the olefin of either the furan or pyrone moieties in the psoralen, resulting in a cyclobutane adduct. This occurs via the triplet state of the psoralen. The product is referred to as a monoadduct, and it alone may be lethal. Upon further irradiation, furan monoadducts can crosslink by undergoing a second cycloaddition reaction involving the olefin of the pyrone moiety, provided there is an adjacent pyrimidine base. Cross links prevent DNA from denaturing rendering it unclonable. If left unirradiated, the resulting DNA can be cloned, since the psoralen will not interfere with the DNA strand separation before cloning.

Having generally described the invention, the following Examples elaborate on the details thereof.

EXAMPLE 1

A. The Optical Chromosome Selection Process:

Step 1. Cell culture and chromosome isolation is well known and described. See, e.g., "Polyamine Buffer For Bivariate Human Flow Cytogenetic Analysis And Sorting," by L. S. Cram et al., Meth. Cell Biol. 33, 377 (1990), and "Univariate Analysis Of Metaphase Chromosomes Using The Hypotonic Potassium Chloride-Propidium Iodide Protocal," by L. S. Cram et al., Meth. Cell Biol. 33, 369 (1990). The isolation process generally results in a chromosome suspension concentration of $\approx 3 \times 10^4$ chromosomes/$\mu$l. It may be possible to make higher concentrations to enabling increased throughput.

Step 2A. Chromosome staining techniques for the purpose of analysis in flow cytogenetics are also well known. The bivariate combination of Hoechst 33258 and chromomycin $A_3$ is commonly used; however, any staining technique which allows separation on the basis of distinctive fluorescent characteristics is usable. See, e.g., Flow Cytometry And Sorting; Wiley-Liss: New York, 1990; pp 824. Step 2B. Chromosome staining for photoinactivation is dependent on the photoinactivation system used.

i. Psoralen derivatives are used as photosensitizers for UV photoinactivation. This procedure is performed under restricted light conditions of >450 nm to prevent unintended photoinactivation. The chromosomes are kept at 4° C. There are several commercially available psoralen derivatives, and several were tested. Naturally occurring derivatives such as 4, 5', 8 trimethylpsoralen are generally hydrophobic, but water-soluble derivatives have been synthesized; e.g., 5-aminomethyl-8-methoxypsoralen. A typical staining procedure is as follows: A 1 $\mu$g psoralen/$\mu$l solution of a chosen psoralen derivative is prepared in water or ethanol, depending on its solubility characteristics. An aliquot of this solution is added to a GM130 chromosome suspension and mixed by gentle pipetting with the final solution being in the range of 5–30 $\mu$g psoralen/ml. This yields approximately 1 psoralen molecule for every 5 DNA bp. The psoralen/chromosome mixture is allowed to "dark" equilibrate at 4° C. overnight; however, shorter incubation times are probably sufficient for intercalation to take place.

ii. Visible-light photoinactivation uses a class of visible light absorbing cyanine, bis-intercalating dimers. This process is done in dim light to minimize unintended photodestruction. Initial experiments were performed with TOTO-1; however, other compounds in this family are expected to be equally effective. In this case, GM130 chromosomes are treated with the intercalator before being stained using the minor groove-binding analytical dyes. TOTO-1 is purchased in a 0.001M solution of DMSO. A typical method for staining is as follows: 20 $\mu$l of the TOTO-1 solution is added to 2 ml of the chromosome suspension to yield a 10 $\mu$M solution thereof. The TOTO-1/chromosome solution is mixed by gentle pipetting. The mixture is "dark" incubated at 4° C. for $\approx$18 hours. See, e.g., G. T. Hirons et al., supra. The estimated TOTO-1 molecule/DNA base pair ratio is $\approx 1/5$. TOTO-1 belongs to a class of benzothiazolium-4-quinolinium dimers. YOYO-1 belongs to a class of benzoxazolium-4-quinoline dimers. Only TOTO-1 has been tested to date, but there is evidence that YOYO-1 would photodamage as well. See, e.g., "Direct Observation of Tube-Like Motion of a Single Polymer Chain," by T. T. Perkins et al., Science 264, 819 (1994).

Step 3. The chromosome suspension was contained in a 1 ml syringe and is delivered to the flow chamber via a syringe pump. The sheath flow is pressure driven although a pump may be used as well. The chromosome sample was hydrodynamically focused within the laminar flow field of the sheath fluid as in traditional flow cytometry. See, e.g., K. L. Albright et al., Am. Chem. Soc. Symp. Series, pages 73–88

(1991). Unlike traditional flow, however, droplet formation is not necessary according to the method of the present invention. This allows for a completely enclosed system which has the advantage that no biological particles can become airborne.

Step 4. Chromosomes stained with Hoechst 33258 and/or Chromomycin $A_3$ are passed through one or two laser beams for analysis. To date, only a single analysis laser has been used (413 nm from a Krypton-ion laser) to excite Chromomycin $A_3$. The fluorescence emission is collected using a 0.6 NA microscope objective, filtered to remove laser wavelengths and detected using a photomultiplier tube (PMT). Signals generated by the PMT are then amplified and integrated, and processed and recorded.

Step 5. The select decision signal normally used to trigger the droplet charging pulse in a conventional flow cytometer apparatus is used to trigger the damage laser beam. The select signal is delayed to allow an unwanted chromosome to reach the damage laser beam location, and the delayed select signal is used to turn on (or off) the damage laser beam, by means of an acoustooptic modulator in the case of a cw laser. It should be mentioned that for the present apparatus the delay time is shorter than that employed in conventional sorting by a factor of between four and ten.

Step 6. While other optical modulation techniques can in principle be used to switch the laser beam on or off to produce optical damage in the unwanted chromosomes, an acoustooptic modulator (AOM) was employed in the present apparatus. An AOM is compact, operates over a broad wavelength range and has switching speeds (~9 MHz) suitable for flow cytometry. The first-order deflection from the AOM is used as the selection/damage beam. While the efficiency for the first-order deflection is only ~80% in this mode (the ON Mode), in the OFF Mode the laser power is zero. By contrast, the zeroth order mode of the AOM does not have a high on/off ratio ($P_{ON}/P_{OFF}$~10:1). Such a poor contrast ratio results in a low level of continuous exposure with consequent photodamage to desired chromosomes. In operation the optical modulator is turned on for a time period that is approximately 1.3 times longer than the transit time of chromosomes through the damage laser beam. The timing is such that the selection beam is turned on well in advance of the chromosome's arrival and remains on after the chromosome has left the selection beam path. This pre- and post-pulse duration will accommodate some of the uncertainty in the arrival time of the chromosomes. However, as described hereinabove, fluorescence detection from the photoinactivation region provides more accurate control of the photoinactivation process. A complementary approach is to permit the selection beam to pass through the flowing stream of particles in its normal condition and to turn it off or deflect it in order to spare a desired chromosome.

Step 7. As stated hereinabove, photoinactivation is achieved using a suitable high power laser beam located downstream of the analytical laser(s). The laser power and wavelength used is dependent on the type of photodamage process. When using psoralen as a photodamaging agent, the 363.1 nm line of an argon ion laser at ≈1.25 W power level is sufficient for photodamage. When working with TOTO-1, photoinactivation is accomplished using the 514 nm line of an Ar-ion laser with a power level of about 3 W.

Step 8. The samples are collected in sterile containers. Size and shape of the container are dependent on experimental conditions, but either polypropylene or siliconized glass tubes are required in order to prevent the chromosomes from adhering to the sides of the containers.

Step 9. In traditional flow sorting, desired chromosomes are physically separated from the unwanted chromosomes. In the optical selection process of the present invention, all chromosomes, both spared and photodamaged, are collected in one receptacle. The output of optical selection has a final concentration of desired chromosomes which is low when compared to traditional flow procedures. Therefore, it is necessary to reduce the volume of sheath fluid. This is achieved by successive centrifugation. Centrifugation is a lengthy and time consuming process. As a result, two alternative processes for chromosome concentration are being considered. The first is a filtration process. The collected chromosome sample would be vacuum filtered onto a 0.2 $\mu$M pore size filter. The cloning process (Step 10, below) begins by lysing the DNA directly from the filter. Filter membrane recovery of material must be optimized to maximize DNA recovery. The second alternative is to dialyze the excess sheath fluid over a highly saturated polyethylene glycol solution. The suspension volume of collected chromosomes would then be reduced due to differences in osmotic pressure. is Although this procedure has not yet been tested in the present method, it has been successful with bare DNA. See, e.g., "A Rapid And Simple Method For The Isolation Of High Molecular Weight Cellular And Chromosome-Specific DNA In Solution Without The Use Of Organic Solvents," by J. L. Longmire, Nucleic Acids Res. 15, 859 (1987).

Step 10. The concentrated chromosomes are then lysed with a detergent solution containing proteinase K. The DNA is digested with a restriction enzyme, dephosphorylated, and purified. After purification, the DNA is ligated to s-Cos-1 cloning arms containing a gene for Kanamycin resistance, packaged using commercial packaging extracts (Stratagene), transfected into DH5αmcr *E. coli* cells, and plated onto NZYDT agar plates containing Kanamycin. Only the clonable DNA ligated to the s-Cos-1 vector arms has Kanamycin resistance, and can grow on the agar plates. The described cloning procedure is not limited by the cells employed; however, if other systems are used, alteration of certain of the steps may be appropriate. For example, dye removal may be necessary. This may be achieved using ethanol washes or a detergent.

Figure 4:
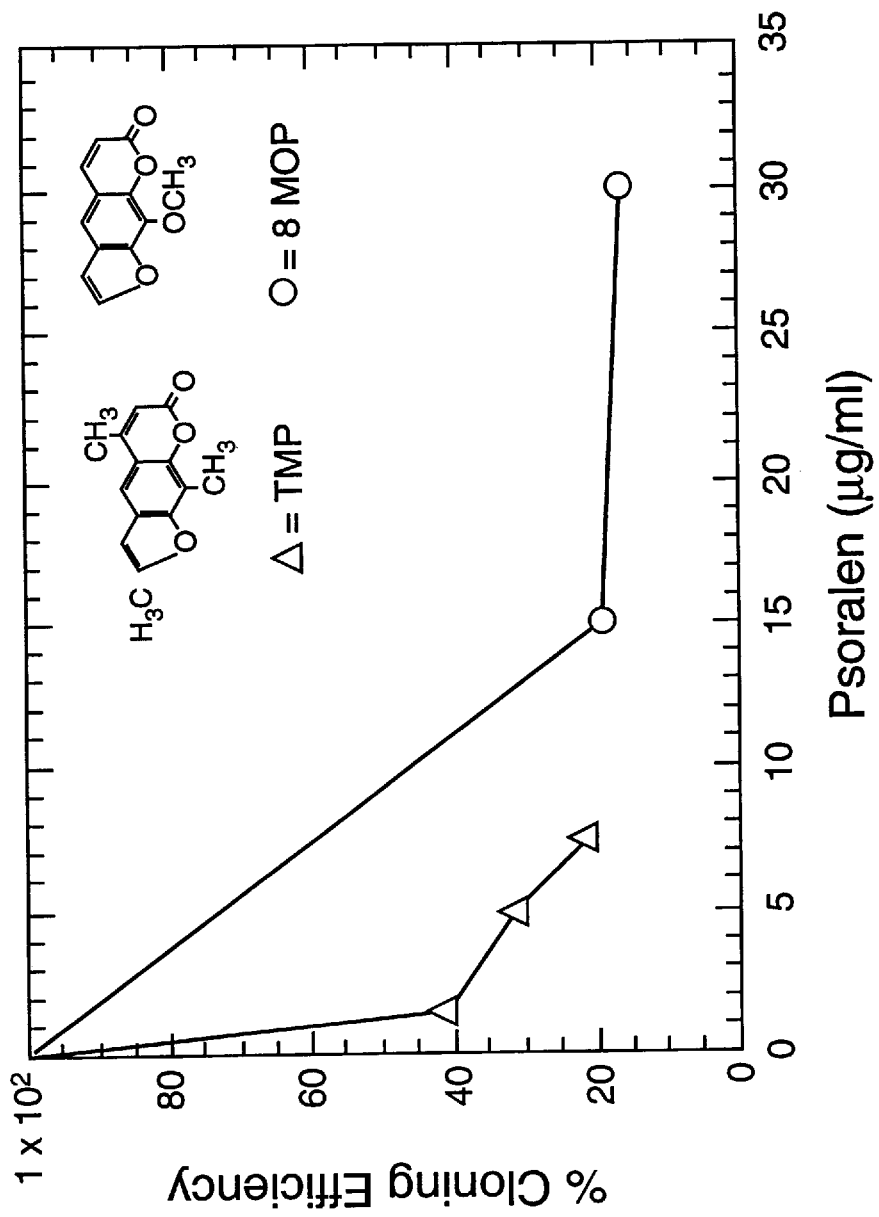
FIG. 4 shows the cloning efficiency of photoinactivated GM130 chromosomal DNA as a function of psoralen concentration.

Spared chromosomes, those not exposed to the high power laser beam, are observed to yield high cloning efficiencies. Photodamaged chromosomes do not clone due to the presence of frequent lethal psoralen/DNA photoadducts. FIG. 4 shows the results of two photodamaging experiments using the psoralen derivatives trimethylpsoralen (TMP) and 8-methoxypsoralen (8-MOP). Cloning efficiencies are measured after chromosomes are irradiated in the presence of varying concentrations of psoralen. In both experiments, significant photoinactivation is achieved; cloning efficiency is reduced by >80% and >85% using 7.5 $\mu$g TMP/ml and 30 $\mu$g 8-MOP/ml, respectively. More recent experiments have yielded cloning reductions >95%. It is desirable to obtain cloning reductions of >99.8% for high-purity chromosome selection.

Psoralen photoinactivation is not as useful, however, when UV analysis is necessary. A UV analytical laser, emitting, for example, at 363.1 nm, excites the Hoechst 33258 stain, but also will excite the psoralen derivative, causing photoadduct formation during analysis. The amount of photoadduct formation depends upon the intensity of irradiation. Therefore, to make optical chromosome selection more versatile, a second system of photoinactivation, which utilizes visible light, has been investigated.

Figure 5:
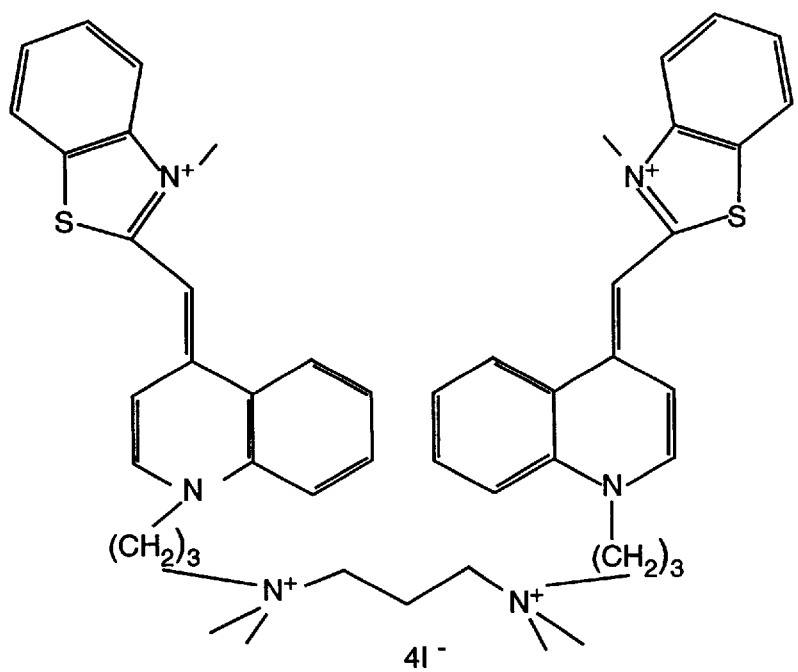
FIG. 5 illustrates the structure of the bis-intercalator TOTO.

This second approach uses a class of cyanine dimers that absorb light in the visible region of the spectrum. These compounds do not absorb the light of currently employed analytical lasers. Furthermore, the absorption of some of these dyes is outside the range of the emission of analytical dyes, thereby reducing the risk of energy transfer during analysis. Among these dyes are YOYO-1 and TOTO-1 which are dimers of the monointercalators (bis-intercalators), oxazole orange and thiazole orange, respectively. A representative structure, that of TOTO-1, is given in FIG. 5. While the binding constants for the monointercalators are on the order of $10^5$–$10^6 M^{-1}$, the binding constants of these bis-intercalators are $10^{11}$–$10^{12} M^{-1}$. Furthermore, the fluorescence yield of the bound dimer species is 1000-fold that of the unbound species See, e.g., "Stable Dye-DNA Intercalation Complexes As Reagents For High Sensitivity Fluorescence Detection," by A. N. Glazer and H. S. Ryes, Nature 359, 859 (1992), "Heterodimeric DNA-Binding Dyes Designed For Energy Transfer: Stability And Applications Of The DNA Complexes," by; S. C. Benson et al., Nucleic Acids Res. 21, 5720 (1993), and H. S. Ryes et al., supra. Recent evidence indicates that irradiation of these dyes results in immediate DNA breakage/damage The mechanism of photobreakage/damage is not well established; however, there is evidence that it is a photo-oxidative process.

Using TOTO-1 as a photosensitizer, photoinactivation has been demonstrated.

Figure 6:
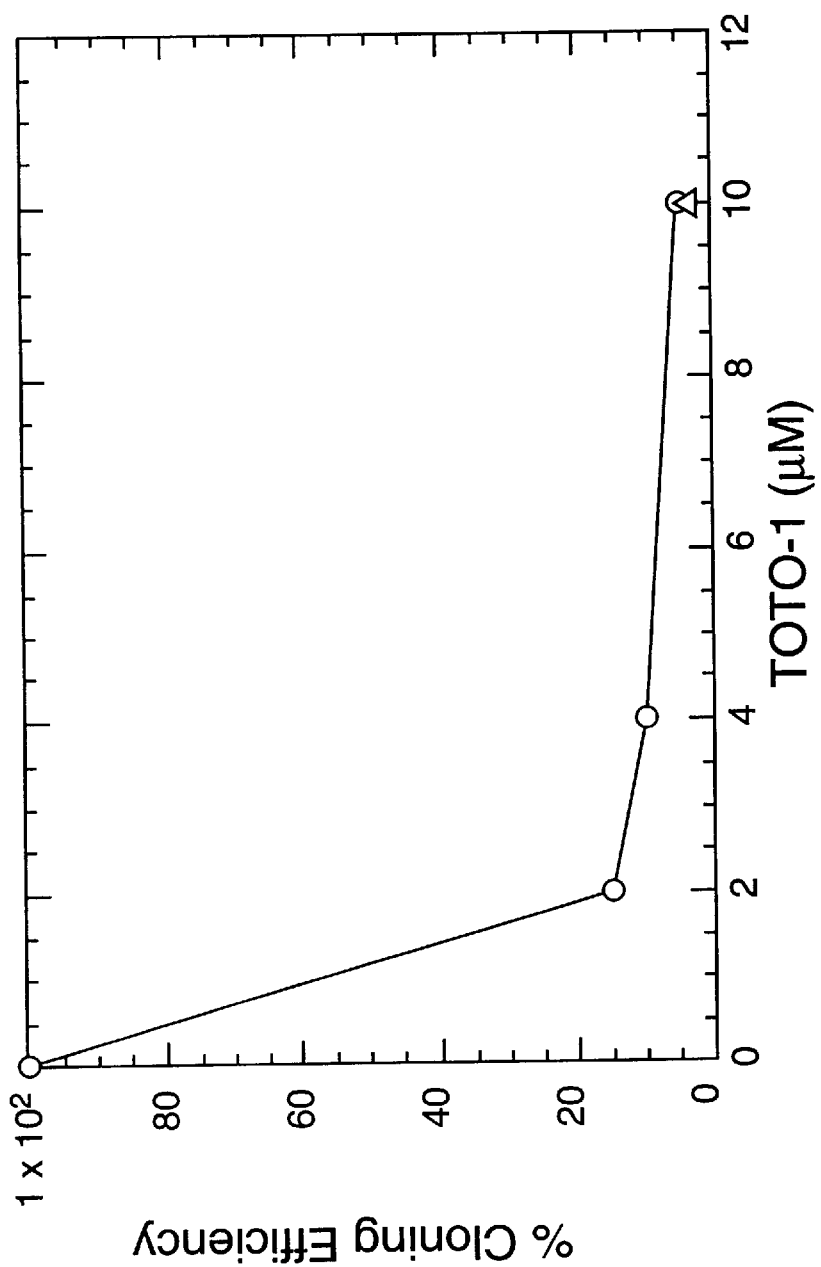
FIG. 6 shows the cloning efficiency of photoinactivated GM130 chromosomal DNA as a function of TOTO-1 concentration.

At TOTO-1 concentrations of 10 $\mu$M, cloning efficiency is reduced by >95% as shown in FIG. 6, hereof (observe the circles). In a second experiment, cloning efficiency is reduced by >98% at a TOTO-1 concentration of 15 $\mu$M (observe lone triangle).

Figure 7:
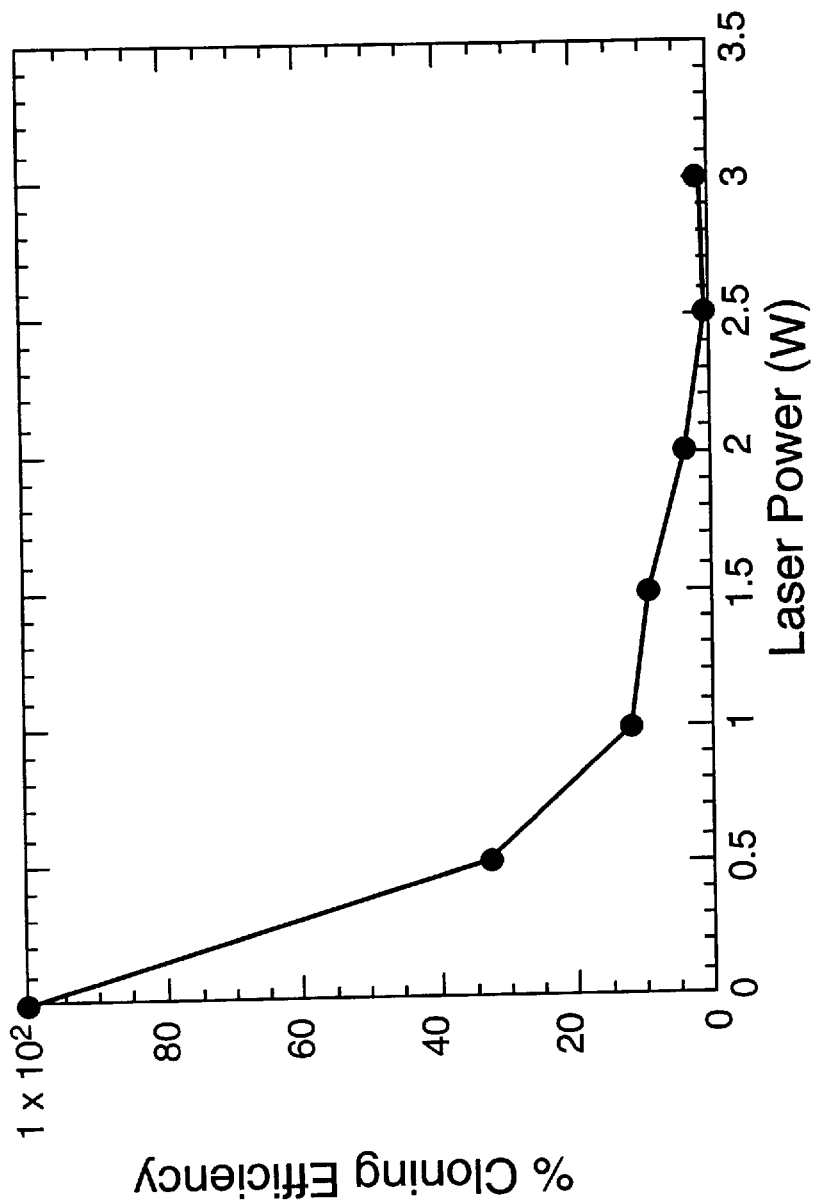
FIG. 7 shows the cloning efficiency of photoinactivated GM130 chromosomal DNA for TOTO-1 as a function of laser power.

FIG. 7 shows the effect of increasing the photoinactivation laser power from 0 W to 2.5 W. Cloning efficiency was reduced by >99%.

EXAMPLE 2

WAV-17 is a rodent/human hybrid cell line containing three no. 21 human chromosomes. Chromosomes from this cell line were isolated and stained with chromomycin $A_3$ and Hoechst 33258. (It is probably sufficient to stain only with the chromomycin $A_3$). The chromosomes are irradiated at 413 nm, exciting only the chromomycin $A_3$, and fluorescence is detected using a photomultiplier tube. Under these analysis conditions, the # 21 chromosome is well-resolved and selection might be achieved by irradiating at 363.1 nm if a psoralen/chromosome complex were to be used.

In preliminary experiments, the WAV-17 chromosomes were bound to TOTO-1 as the photoinactivating molecule. Analysis was performed at 413 nm, and photoinactivation at 514 nm. Once selected, the no. 21 chromosomes are cloned and the are probed for both human and rodent DNA to determine purity. The observed high percentages of human DNA indicate a high degree of selection (85–95%). Such experiments permit library construction; that is, optical selection of a specific chromosome is possible.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for rendering unclonable a subpopulation of DNA fragments in a suspension of DNA fragments containing the subpopulation, each of said fragments being bonded to at least one photoinactivating species, said invention comprising in combination:

(a) means for detecting the presence of selected DNA fragments from the subpopulation in a flowing stream containing the suspension of DNA fragments, thereby generating signals in response to the presence of the DNA fragments from the subpopulation in the flowing stream;

(b) means, downstream from said detecting means and responsive to the generated signals, for producing pulses of light directed through a region of the flowing stream through which individual DNA fragments pass and which are absorbed by the at least one photoinactivating molecule bound to individual DNA fragments, whereby individual selected DNA fragments in the subpopulation thereof in the flowing stream are inactivated and cannot be cloned; and (c) means for measuring the fluorescence intensity from the selected DNA fragments which are inactivated by the pulses of light from said light pulse producing means, such that the pulses of light may be accurately timed to substantially coincide with the arrival of the individual selected DNA fragments from the subpopulation thereof in the region of the flowing stream in which the pulses of light are directed.

2. The apparatus for rendering unclonable a subpopulation of DNA fragments in a suspension of DNA fragments containing the subpopulation as described in claim 1, further comprising means for hydrodynamically focusing the suspension of stained and bound DNA fragments within the laminar flow field of the sheath fluid in a flow cytometer.

3. The apparatus for rendering unclonable a subpopulation of DNA fragments in a suspension of DNA fragments containing the subpopulation as described in claim 1, wherein each DNA fragment in the suspension is stained with at least one analytic fluorescent dye, and wherein said means for detecting the presence of DNA fragments from the subpopulation in the flowing stream comprises means for generating a beam of light selected to excite the at least one analytic fluorescent dye thereon, thereby producing fluorescence emission from the at least one analytic fluorescent dye thereon, and means for measuring the intensity of the fluorescence emission from the at least one analytic fluorescent dye, whereby individual DNA fragments from the subpopulation are identified.

* * * * *